(12) United States Patent
Kilgard et al.

(10) Patent No.: US 10,029,094 B2
(45) Date of Patent: Jul. 24, 2018

(54) METHODS AND SYSTEMS FOR THERAPY OF MULTIPLE SCLEROSIS

(71) Applicant: The Board of Regents of the University of Texas System, Austin, TX (US)

(72) Inventors: Michael P. Kilgard, Richardson, TX (US); Robert L. Rennaker, II, Sachse, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/947,797

(22) Filed: Nov. 20, 2015

(65) Prior Publication Data

US 2016/0144176 A1    May 26, 2016

Related U.S. Application Data

(60) Provisional application No. 62/082,403, filed on Nov. 20, 2014.

(51) Int. Cl.
*A61N 1/00* (2006.01)
*A61N 1/36* (2006.01)
*G06F 19/00* (2018.01)
*G09B 19/00* (2006.01)

(52) U.S. Cl.
CPC ..... *A61N 1/36025* (2013.01); *G06F 19/3481* (2013.01); *G09B 19/00* (2013.01)

(58) Field of Classification Search
CPC .................................................. A61N 1/36025

USPC .............................................................. 607/3
See application file for complete search history.

(56) References Cited

U.S. PATENT DOCUMENTS

| 4,702,254 A | 10/1987 | Zabara |
| 8,666,501 B2 | 3/2014 | Kilgard et al. |
| 2003/0144709 A1 | 7/2003 | Zabara et al. |

(Continued)

OTHER PUBLICATIONS

Marrosu F et al. (2007) Vagal nerve stimulation improves cerebellar tremor and dysphagia in multiple sclerosis. Multiple Sclerosis 13:1200-1202.

(Continued)

*Primary Examiner* — Nadia A Mahmood
(74) *Attorney, Agent, or Firm* — Parker Highlander PLLC

(57) ABSTRACT

A method for treating neural deficits resulting from multiple sclerosis, involving assessing a subject's motor, sensory, cognitive, or emotional deficits caused by multiple sclerosis; selecting a rehabilitative task based said deficits; determining the subject's acceptable performance threshold for the rehabilitative task; and providing a paired training therapy. The paired training therapy comprises having the subject to perform a trial of the rehabilitative task; classifying the subject's performance on the trial as either acceptable or unacceptable, wherein an acceptable performance is performance at or above the subject's acceptable performance threshold, and an unacceptable performance is performance below the subject's acceptable performance threshold; and reinforcing acceptable performance by selectively stimulating the subject's vagus nerve after completion of the acceptable performance.

20 Claims, 6 Drawing Sheets

(56) References Cited

U.S. PATENT DOCUMENTS

| | | |
|---|---|---|
| 2007/0265489 A1* | 11/2007 | Fowler .............. A61N 1/36082 600/12 |
| 2010/0003656 A1 | 1/2010 | Kilgard et al. |
| 2010/0004705 A1 | 1/2010 | Kilgard et al. |
| 2010/0004717 A1 | 1/2010 | Kilgard et al. |
| 2013/0072996 A1 | 3/2013 | Kilgard et al. |
| 2014/0058189 A1 | 2/2014 | Stubbeman |

OTHER PUBLICATIONS

Hays, S.A., Rennaker R.L., Kilgard M.P. (2014) Targeting Plasticity with Vagus Nerve Stimulation to Treat Neurological Disease. In Changing Brains—Applying Brain Plasticity to Advance and Recover Human Ability, Progress in Brain Research, 207:275-99, 2014.

Ritvo P.G. et al. "Multiple Sclerosis Quality of Life Inventory: A User's Manual." Retrieved Nov. 6, 2015, from www.nationalmssociety.org/NationalMSSociety/media/MSNationalFiles/Brochures/MSQLI_-A-User-s-Manual.pdf.

* cited by examiner

Matlab code for Figs. 2-4:

```
clf, hold on
d=(randn(1000000, 1)*10)+120;
[h, hh]=hist(d, 100);
plot(hh, h/10000, 'ko-')
f=find(hh>median(d))
plot(hh(f), h(f)/10000, 'r*-')
ylabel('Percent of trials'), xlabel('Force (grams)')
title('VNS delivered on best trials (red stars)')

clf, hold on
d=(randn(100, 1)*10)+120;
s=(randn(100, 1)*100)+350;
plot(d, s, 'ko')
ylabel('Latency (milliseconds) '), xlabel('Force
(grams)')
e=d./s; %ratio of grams over msec
e=((d-min(d))/range(d))- ((s-min(s))/range(s))
f=find(e>median(e))
plot(d(f), s(f), 'r*')
title('VNS delivered on trials that are strong and fast
(red stars) - Ratio')
title('VNS delivered on trials that are strong and fast
(red stars) - Average Percentile')
```

Fig. 5

METHODS AND SYSTEMS FOR THERAPY OF MULTIPLE SCLEROSIS

CROSS-REFERENCE TO RELATED APPLICATION

The present application claims benefit of and priority to U.S. Provisional Patent Application Ser. No. 62/082,403 filed on Nov. 20, 2014 entitled "Methods and Systems for Therapy of Multiple Sclerosis Patients," the entire contents of which are hereby incorporated by reference herein.

BACKGROUND

This invention relates to the field of therapy and rehabilitation for neural degeneration. This invention is also related to at-home rehabilitation and therapy for improvement of synaptic plasticity in multiple sclerosis patients.

Multiple sclerosis (MS) involves the degradation of a patient's brain networks via demyelination. The patient's immune system attacks the central nervous system, breaking down the fatty myelin sheath which protects a nerve fiber. Myelin breakdown (demyelination) disrupts a nerve's action potential—its fine-tuned ability to receive and convey a stimulus. Disruption of the action potential results in disruption of synaptic plasticity—the ability of synapses to strengthen or weaken over time.

Synaptic plasticity is highly sensitive to action potential timing. The difference between 10 and 50 milliseconds in action potential can be the difference between long term potentiation (strengthening) and long term depression (weakening).

Some options available to patients suffering from decreased synaptic plasticity include brain training and rehabilitation. Unfortunately, the effectivity of brain training has not been conclusively established. Traditional rehabilitation techniques, on the other hand, are expensive and require the intervention of professionally trained therapists and medical professionals.

Existing methods specifically target plasticity to treat neurological disease. Deep brain stimulation, transcranial magnetic stimulation, optogenetic stimulation, or intensive repeated training could potentially trigger sufficient neuromodulatory release during experience to induce therapeutic plasticity.

Furthermore, stimulation of the vagus nerve paired with behavioral experience may also drive specific forms of neural plasticity. Vagus nerve stimulation (VNS) engages multiple neuromodulatory systems and can be precisely temporally controlled. Additionally, VNS is a safe and approved method currently being used in over 60,000 patients for management of intractable epilepsy and depression. Recent studies have demonstrated that VNS paired with sensory, motor, or cognitive training can drive specific forms of cortical plasticity that result in behaviorally relevant changes. As a result, VNS applied as a targeted plasticity therapy offers the potential to treat sensory, motor, and cognitive dysfunction.

BRIEF SUMMARY OF THE INVENTION

Accordingly, an example embodiment of the inventions is a method for treating neural deficits resulting from multiple sclerosis. The method involves assessing a subject's motor, sensory, cognitive, or emotional deficits caused by multiple sclerosis; selecting a rehabilitative task based on the subject's deficits; determining an acceptable performance threshold for the subject on the rehabilitative task; and providing a paired training therapy. The paired training therapy comprises having the subject to perform a trial of the rehabilitative task; classifying the subject's performance on the trial as either acceptable or unacceptable, wherein an acceptable performance is performance at or above the subject's acceptable performance threshold, and an unacceptable performance is performance below the subject's acceptable performance threshold; and reinforcing acceptable performance by selectively stimulating the subject's vagus nerve after completion of the acceptable performance.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 5 shows the Matlab code used to generate the plots in FIGS. 2-4.

DETAILED DESCRIPTION OF THE INVENTION

Figure 1A:
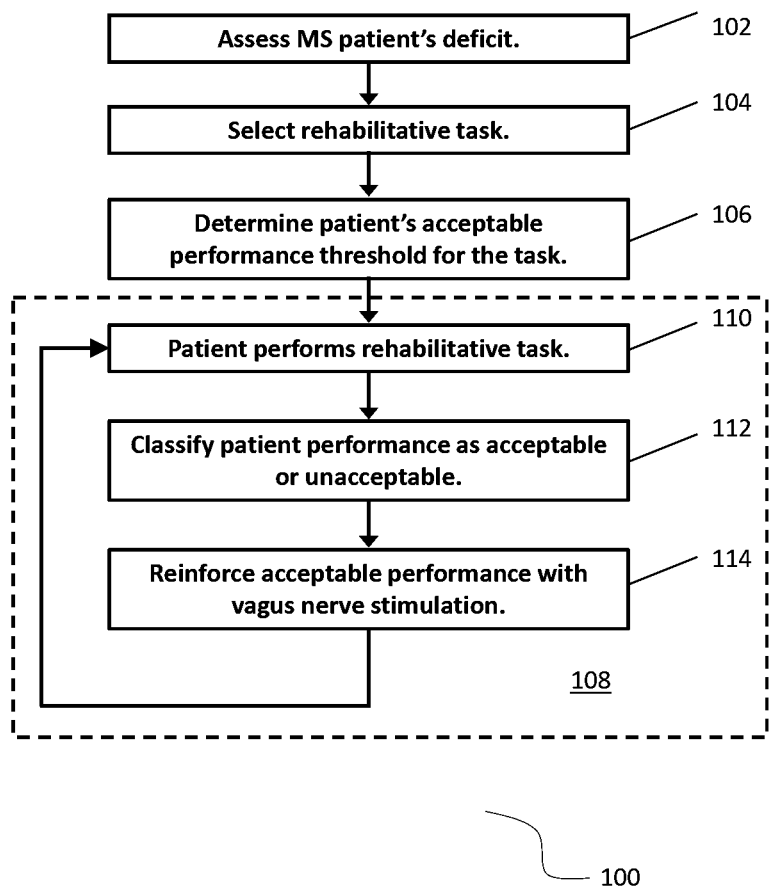
FIG. 1A shows a method for treating neural deficits resulting from multiple sclerosis using a fixed acceptable performance threshold, in accordance with one embodiment of the invention.
Figure 1B:
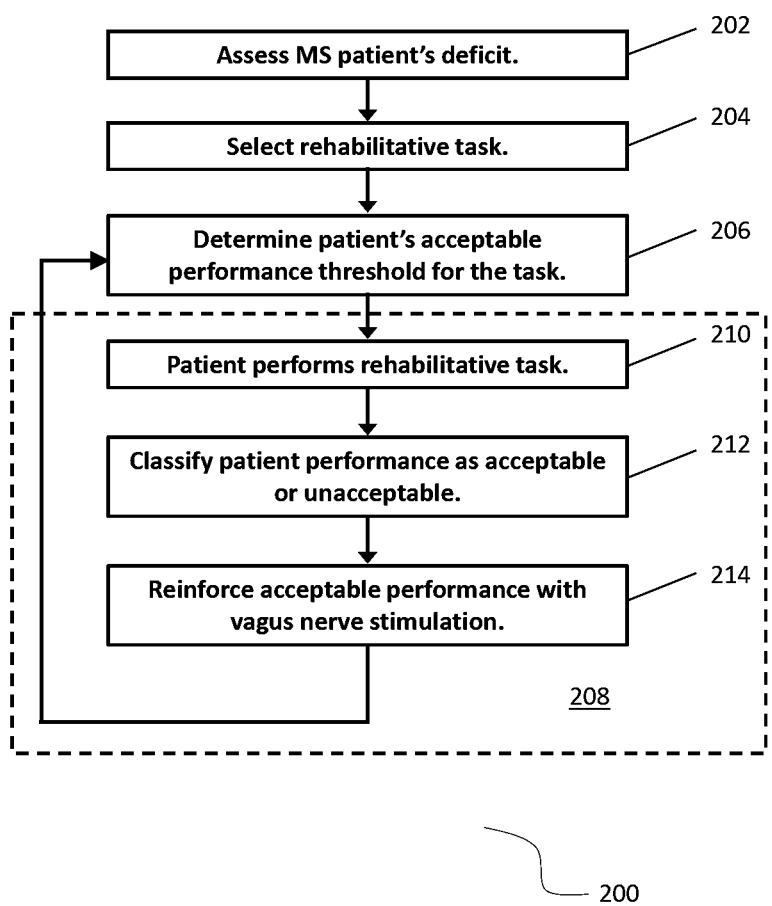
FIG. 1B shows a variant of the method shown in FIG. 1A, utilizing an adaptive acceptable performance threshold, in accordance with one embodiment of the invention.

FIGS. 1A and 1B show methods 100 and 200 for treating neural deficits resulting from multiple sclerosis, in accordance with one embodiment of the invention. The methods 100 and 200 begin by assessing a subject's motor, sensory, cognitive, or emotional deficits 102 and 202, as caused by multiple sclerosis.

According to an embodiment of the invention, assessment of a subject's sensory deficit may include assessment for hypoesthesia, pain, visual function problems, auditory function problems, and difficulties with coordination and/or balance. Assessment for pain may be performed using the MOS Pain Effects Scale (PES); assessment for visual function problems may be performed using the Impact of Visual Impairment Scale (IVIS); and assessment for auditory function problems may utilize a Speech-in-Noise test (also known as the interrupted noisemaker test). The subject may be a mammalian subject or a human subject such as, for example, a patient.

According to an embodiment of the invention, assessment of a subject's motor deficit may be performed using the 9-Hole Peg Test (9-HPT). According to another embodiment of the invention, assessment of a subject's motor deficit may also include assessment for weakness, spasms, dysarthria, dysphagia, fatigue, and incontinence. Assessment for incontinence may involve assessment of bowel function utilizing, for example, the Bowel Control Scale (BWCS) and assessment of bladder function utilizing, for example, the Bladder Control Scale (BLCS).

Assessment of cognitive deficits may include assessment of memory, attention, processing speed, visual-spatial abilities, and executive function.

Assessment of a subject's emotional deficit may involve an assessment of a subject's mental health such as, for example, a Mental Health Inventory (MHI).

The methods 100 and 200 then proceed to selecting a rehabilitative task 104 and 204 based on the subject's deficits. These rehabilitative tasks may physical therapy tasks, occupational therapy, speech therapy, and cognitive rehabilitation.

Non-limiting examples of rehabilitative tasks include cognitive training (such as BRAINHQ, a brain training software which provides exercises to improve attention, brain speed, memory, people skills, intelligence, and navigation) for deficiencies in cognitive function; auditory training (such as the Auditory: Brain Fitness program) for auditory function problems; visual training (such as INSIGHT, a software which provides exercises to expand divided attention and improve visual precision, visual working memory, useful field of view, and visual processing speed); for visual function problems; biofeedback bowel control training and biofeedback bladder control training for bowel and bladder control problems, respectively; tactile discrimination training for pain; facial discrimination training for deficiencies in emotional function, and physical therapy for deficiencies in motor function.

Non-limiting examples of physical therapy tasks for a subject with multiple sclerosis include physical exercise, gait training for walking problems, pelvic exercises, and training with mobility devices such as canes.

Non-limiting examples of occupational therapy for subjects with multiple sclerosis include cognitive training or cognitive retraining for deficiencies in cognitive function.

Non-limiting examples of speech therapy for subjects with multiple sclerosis include mouth and tongue exercises, and enunciation exercises.

Non-limiting examples of cognitive rehabilitation for subjects with multiple sclerosis include memory exercises, puzzles, and games. According to one embodiment of the invention, the rehabilitative task may be administered using a personal computing device.

Additional information regarding the various methods for assessing sensory, motor, cognitive, and emotional deficiencies of MS subjects and rehabilitative tasks for the aforementioned deficiencies may be obtained from the Multiple Sclerosis Quality of Life Inventory: A User's Manual, which is incorporated herein by reference.

Once the rehabilitative task is selected, the methods 100 and 200 proceed to determining an acceptable performance threshold level 106 and 206 for the task. The acceptable performance threshold level may vary depending on the results of the assessment 102 and 202 of the subject's motor, sensory, and cognitive deficits. FIG. 1A shows that, according to an embodiment of the invention, the acceptable performance threshold may be fixed such as, for example, at the median performance level based on a prior set of tasks.

FIG. 1B shows that, according to another embodiment of the invention, the acceptable performance threshold may be an adaptive threshold. That is, the acceptable performance threshold is a moving target and varies depending on the subject's previous performance. For example, the threshold may be set at the median of the subject's past performance. The threshold may also be set at the median of a selected number of the subject's most recent trials, such as the subject's last 10 trials. The adaptive threshold may also be set at the mean or median of the subject's trials after outlying trials have been removed.

The advantages of an adaptive threshold are that: 1) for any level of disability, this approach guarantees that every subject receives VNS, and 2) the delivery of VNS provides additional information that selectively reward neurons that are active during successful trials, which over pushes the entire network toward better performance.

According to an embodiment of the invention, the adaptive threshold may be time-dependent. In one embodiment, the acceptable performance threshold includes completion within a predetermined time limit. Completion of the rehabilitative task after the time limit expires would render the performance unacceptable. In another embodiment, both time (latency from a cue or from first contact) and another factor (i.e. force applied) are combined to set an acceptable performance threshold. The combination may be the ratio of the two factors (i.e. force/time). The combination may also be any non-linear operation to weight between the two factors. For more complex tasks like buttoning a shirt or reading a passage of text, many factors could be combined to make a performance index, for which there will be an acceptable performance threshold.

Once an acceptable performance threshold has been determined, the methods 100 and 200 proceed to providing a paired training therapy 108 and 208. The paired training therapy involves first having the subject perform a trial of the rehabilitative task 110; second, classifying the subject's performance on the trial as either acceptable or unacceptable 112; and third, reinforcing acceptable performance at a trial by selectively stimulating the subject's vagus nerve after completion of the acceptable performance 114 and 214.

A performance is considered acceptable if the performance meets or exceeds the subject's acceptable performance threshold. On the other hand, a performance is considered unacceptable if the performance is does not meet the subject's acceptable performance threshold level.

According to an embodiment of the invention, selectively stimulating the subject's vagus nerve may involve applying an electric pulse train using a subcutaneous device. The subject's vagus nerve may also involve applying an electric pulse train using a transcutaneous device. Such a device may utilize magnetic pulses or ultrasound. One skilled in the art may identify suitable devices for stimulating the vagus nerve, including commercially available devices and experimental devices.

The electric pulse train may have a current amplitude of 0.1 to 2.0 milliamps (mA), such as between 0.4 to 1.0 mA, or between 0.7 to 0.9 mA, such as at around 0.8 mA. The electric pulse train may also have a duration of 30 to 5000 milliseconds (ms), such as 125 to 2000 ms, 400 to 600 ms, or 500 ms. For example, the electric pulse train with a duration of 500 ms typically consists of 15 pulses at 30 hz. An increase in pulse train duration would be associated with an increase in the number of pulses or a decrease in frequency. Conversely, a decrease in pulse train duration would be associated with a decrease in the number of pulses or an increase in frequency.

According to another embodiment of the invention, the subject's vagus nerve may be stimulated within 3,000 milliseconds (ms) or 3 seconds of completion of the acceptable performance, preferably within 500 milliseconds, such as within 50 milliseconds of completion of the acceptable performance.

According to an embodiment of the invention, performance of the rehabilitative task 110 and 210 may include partial performance of the task. That is, classification of subject performance 112 and 212 and stimulation of the subject's vagus nerve 114 and 214 may be undertaken before the rehabilitative task is completed. For example, certain types of physical therapy may require moving an object from a first position to a second position, and then back to the first position (e.g., turning a knob; lifting weights). Classification of the subject's performance 114 and 214 and stimulation of the vagus nerve 116 and 216 may be undertaken at a variety of therapist-selected points in the task (i.e., when the knob is fully turned in one direction; when the weight is lifted halfway to the second position).

According to an embodiment of the invention, the paired training therapy may be repeated multiple times. The number of repetitions may be a therapist-prescribed finite limit. The number of repetitions may also depend on the trajectory of a subject's rehabilitation. For example, a rapidly-improving subject may require a change in therapy and a small number of repetitions in a relatively easy task. In such a case, the paired training therapy for a specific rehabilitative task may cease once large fraction of a subject's recent trials are considered acceptable performances.

Figure 2:
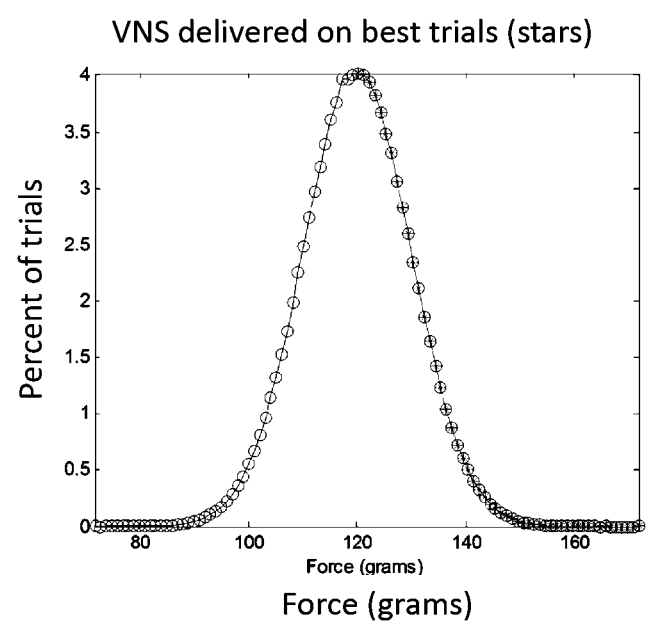
FIG. 2 shows a plot for a first example embodiment of the invention involving a set of hypothetical strength trials in rats, wherein the acceptable performance threshold is set at a force of 120 g for the trials.

FIG. 2 shows a plot for a first example embodiment of the invention involving a set of motor rehabilitation tasks in rats. In this example, the task is the isometric force task and the acceptable performance threshold is set at a force of 120 g for the trials. The 120-g performance threshold is derived from a prior set of strength trials (not shown, assuming identical data set), by calculating the median for said prior set of trials. The starred circles represent trials that meet or exceed the acceptable performance threshold and for which vagus nerve stimulation is delivered. This plot demonstrates a hypothetical, ideal case, wherein the prior and current sets of strength trials have the same median.

Figure 3:
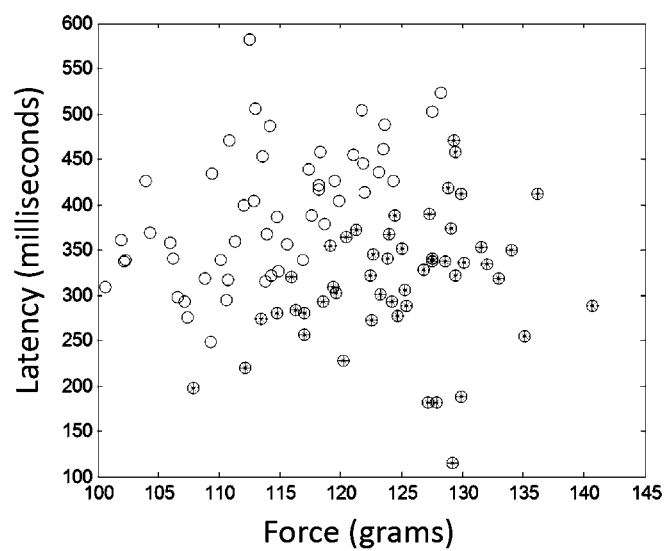
FIG. 3 shows a plot for a second example embodiment of the invention involving a set of hypothetical strength trials in rats, wherein the acceptable performance threshold is set at a median Force/Latency ratio of the data set.

FIG. 3 shows a plot for a second example embodiment of the invention involving a set of motor rehabilitation tasks in rats. In this example, the task is the isometric force task and the acceptable performance threshold incorporates both the maximum force used by a subject mouse (force) and the time elapsed before that maximum force was reached (latency). In this example, the acceptable performance threshold is set at the median Force/Latency ratio of the data set. This performance threshold is derived from a prior set of strength trials (not shown, assuming identical data set), by calculating the median Force/Latency ratio for said prior set of trials. The starred circles represent trials that meet or exceed the acceptable performance threshold and for which vagus nerve stimulation is delivered. This plot demonstrates a hypothetical, ideal case, wherein the prior and current sets of strength trials have the same median.

Figure 4:
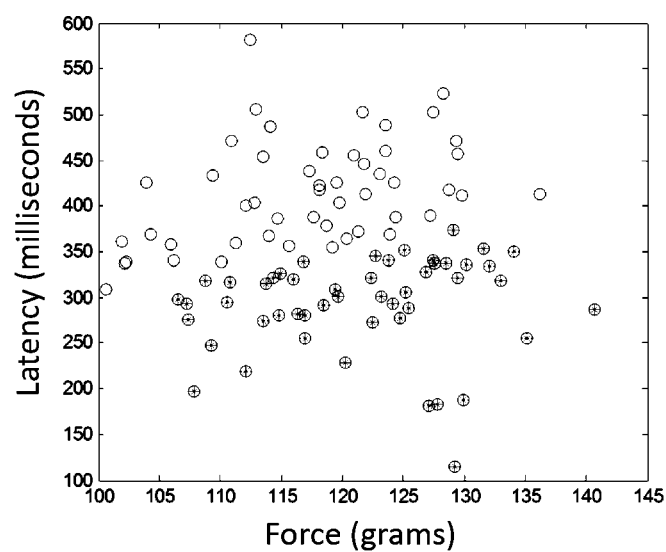
FIG. 4 shows a plot for a fourth example embodiment of the invention involving a set of hypothetical strength trials in rats, wherein the acceptable performance threshold is set at the 50th percentile of Force/Latency ratios of the trials.

FIG. 4 shows a plot for a fourth example embodiment of the invention involving a set of motor rehabilitation tasks in rats. In this example, the task is the isometric force task, again with performance measured using both force and latency. The acceptable performance threshold is set at the 50th percentile of Force/Latency ratios of the trials. This performance threshold is derived from a prior set of strength trials (not shown, assuming identical data set), by calculating the 50th percentile of Force/Latency ratios for said prior set of trials. The starred circles represent trials that meet or exceed the acceptable performance threshold and for which vagus nerve stimulation is delivered. This plot demonstrates a hypothetical, ideal case, wherein the prior and current sets of strength trials have the same median.

FIG. 5 shows the Matlab code used to generate the plots in FIGS. 2-4.

The descriptions of the various embodiments of the present invention have been presented for purposes of illustration, but are not intended to be exhaustive or limited to the embodiments disclosed. Modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for treating neural deficits resulting from multiple sclerosis, the method comprising:
    assessing a subject's motor, sensory, cognitive, or emotional deficits caused by multiple sclerosis;
    selecting a rehabilitative task based on the subject's deficits;
    determining an acceptable performance threshold for the subject on the rehabilitative task; and
    providing a paired training therapy, wherein the paired training therapy comprises
        having the subject to perform a trial of the rehabilitative task;
        classifying the subject's performance on the trial as either acceptable or unacceptable, wherein an acceptable performance is performance at or above the subject's acceptable performance threshold, and an unacceptable performance is performance below the subject's acceptable performance threshold; and
        reinforcing acceptable performance by selectively stimulating the subject's vagus nerve after completion of the acceptable performance.

2. The method of claim 1, wherein selectively stimulating the subject's vagus nerve involves stimulating the subject's vagus nerve by applying an electric pulse train using a subcutaneous device.

3. The method of claim 2, wherein the electric pulse train includes an electric pulse with a current amplitude of 0.1 to 2.0 milliamps and a duration of 30 to 5000 milliseconds.

4. The method of claim 2, wherein the electric pulse train includes an electric pulse with a current amplitude of 0.1 to 2.0 milliamps and a duration of 125 to 2000 milliseconds.

5. The method of claim 2, wherein the electric pulse train includes an electric pulse with a current amplitude of 0.4 to 1.0 milliamps and a duration of 125 to 2000 milliseconds.

6. The method of claim 2, wherein the electric pulse train includes an electric pulse with a current amplitude of 0.7 to 0.9 milliamps and a duration of 125 to 2000 milliseconds.

7. The method of claim 2, wherein selectively stimulating the subject's vagus nerve also includes stimulating the vagus nerve within 3 seconds after completion of the acceptable performance.

8. The method of claim 2, wherein selectively stimulating the subject's vagus nerve also includes stimulating the vagus nerve within 500 milliseconds after completion of the acceptable performance.

9. The method of claim 2, wherein selectively stimulating the subject's vagus nerve also includes stimulating the vagus nerve within 50 milliseconds after completion of the acceptable performance.

10. The method of claim 2, wherein stimulating the subject's vagus nerve immediately after above average performance includes stimulating the vagus nerve between 125 ms and 2000 ms after completion of the acceptable performance.

11. The method of claim 1, wherein the rehabilitative task is selected to address the subject's deficits.

12. The method of claim 1, wherein the rehabilitative task is a physical therapy task.

13. The method of claim 1, wherein the rehabilitative task an occupational therapy task.

14. The method of claim 1, wherein the rehabilitative task is a speech therapy task.

15. The method of claim 1, wherein the rehabilitative task is a cognitive rehabilitation task.

16. The method of claim 1, further comprising repeating the paired training therapy.

17. The method of claim 1, wherein the rehabilitative task is administered using a personal computing device.

18. The method of claim 1, wherein the acceptable performance threshold is adaptive.

19. The method of claim 1, wherein the subject is a patient.

20. The method of claim 1, wherein selectively stimulating the subject's vagus nerve involves stimulating the subject's vagus nerve by applying an electric pulse train using a transcutaneous device.

* * * * *